United States Patent
Komatsu et al.

(10) Patent No.: US 6,774,987 B2
(45) Date of Patent: Aug. 10, 2004

(54) SURFACE INSPECTION METHOD, SURFACE INSPECTION APPARATUS, AND RECORDING MEDIUM AND DATA SIGNAL FOR PROVIDING SURFACE INSPECTION PROGRAM

(75) Inventors: Koichiro Komatsu, Setagaya-ku (JP); Takeo Oomori, Katsushika-ku (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 10/661,620

(22) Filed: Sep. 15, 2003

(65) Prior Publication Data

US 2004/0063232 A1 Apr. 1, 2004

Related U.S. Application Data

(63) Continuation of application No. 09/481,503, filed on Jan. 12, 2000, now abandoned.

(30) Foreign Application Priority Data

Jan. 13, 1999 (JP) .......................................... 11-006242

(51) Int. Cl.$^7$ ............................................. G01N 21/88
(52) U.S. Cl. ..................................... 356/73; 356/237.4
(58) Field of Search ............................... 356/73, 237.4, 356/237.5, 394

(56) References Cited

U.S. PATENT DOCUMENTS

| | | | |
|---|---|---|---|
| 4,881,268 A | 11/1989 | Uchida et al. | ................ 356/71 |
| 5,497,234 A | 3/1996 | Haga | ....................... 356/237.5 |
| 5,777,729 A | 7/1998 | Aiyer et al. | |
| 6,166,393 A | 12/2000 | Paul et al. | ............... 356/237.5 |
| 6,201,601 B1 | 3/2001 | Vaez-Iravani et al. | ... 356/237.4 |
| 6,222,624 B1 | 4/2001 | Yonezawa | ............... 356/237.4 |

*Primary Examiner*—Richard A. Rosenberger
(74) *Attorney, Agent, or Firm*—Oliff & Berridge, PLC

(57) ABSTRACT

A surface inspection method for inspecting a pattern formed at a surface of a test piece, includes: a first step in which a plurality of inspection conditions that are different from each other are set; a second step in which light from the surface of the test piece is detected by irradiating illumination light onto the surface of the test piece under each of the plurality of inspection conditions; a third step in which a plurality of sets of detection information corresponding to the plurality of inspection conditions are generated based upon the detected light; a fourth step in which a logical OR of the plurality of sets of detection information is obtained; and a fifth step in which a decision is made as to whether or not the pattern at the surface of the test piece is acceptable based upon results of the logical OR.

16 Claims, 10 Drawing Sheets

SURFACE INSPECTION METHOD, SURFACE INSPECTION APPARATUS, AND RECORDING MEDIUM AND DATA SIGNAL FOR PROVIDING SURFACE INSPECTION PROGRAM

This is a Continuation of U.S. application Ser. No. 09/481,503 filed Jan. 12, 2000, now abandoned which claims the benefit of Japanese Patent Application No. 11-006242, filed Jan. 13, 1999. The disclosures of these prior applications are incorporated by reference herein in their entireties.

INCORPORATION BY REFERENCE

The disclosures of the following priority application are herein incorporated by reference: Japanese Patent Application No. 11-6242 filed Jan. 13, 1999.

BACKGROUND OF THE INVENTION

1. Field of the Invention

The present invention relates to a surface inspection method and a surface inspection apparatus employed to detect, for instance, foreign matter (or contamination) adhering to a minute cyclical pattern formed on the surface of a test piece, scarring in such a pattern, or defects such as line width error or film thickness error in the pattern, that are particularly ideal in the inspection of semiconductor wafers such as ASICs, liquid crystal display panels and the like. In addition, the present invention relates to a recording medium and a data signal that provides a surface inspection program.

2. Description of the Related Art

When manufacturing semiconductor devices, liquid crystal display panels, thin film magnetic heads or the like, it is necessary to implement an inspection to detect the presence/absence of foreign matter or the like adhering to a fine pattern formed on the surface of a substrate such as a semiconductor wafer or a liquid crystal panel or defects such as line width errors in the pattern at the stage at which a circuit pattern in a specific layer has been formed, at the ultimate stage at which the circuit patterns in all the layers have been formed and the like. In the prior art, this type of inspection is conducted by an inspector by illuminating the test substrate with illumination light originating from a light source referred to as a macro illumination device and visually observing the scattered light and the diffracted light originating from the surface of the test substrate.

However, such a visual inspection is greatly affected by factors such as the skill and experience of the inspector and the inspection environment. Thus, Japanese Laid Open Patent Publication No. H8-75661 discloses an inspection apparatus that identifies foreign matter and the like by receiving reflected light (scattered light and diffracted light) from a test substrate at a photoelectric detector via a light-receiving optical system and performing image processing on a detection signal output by the photoelectric detector.

As explained above, in the inspection apparatus in the prior art, defects and the like in a pattern on the test substrate are detected by receiving light reflected from the test substrate along a specific direction. Thus, the distribution of defects and the like can be detected promptly over the entire surface of the pattern under inspection, since the diffracted light coming from the entire surface of the test substrate can be received at once by the light-receiving optical system as long as the pattern can be regarded as one type of cyclical pattern having a specific, almost fixed pitch over the entire surface of the substrate, as in a DRAM for instance.

However, in recent years, it has become necessary to conduct inspections on devices constituted of numerous different circuit patterns having different arrangements formed in individual chip areas (shot areas) on a semiconductor wafer, such as the so-called logic-ICs and AS ICs (Application Specific ICs). In such a device, a plurality of types of cyclical patterns having different pitches from each other formed on the test substrate must be inspected. Thus, since only the diffracted light from the cyclical pattern having a specific pitch can be obtained if the optical system has a specific positional relationship relative to the test substrate, there is a concern that defects and the like of cyclical patterns having pitches other than the specific pitch may not be detected.

In addition, since a pattern formed on the surface of the test substrate is achieved by etching or CVD method, the pattern on a semiconductor substrate under the process is formed by thin films for resist. Furthermore, already formed patterns are piled in several layers. As a result, the intensity of the diffracted light may become reduced by the thin film interference and the like. Because of this, if an inspection apparatus in the prior art is set to receive only the diffracted light of a specific order, the diffracted light quantity becomes reduced, which poses a problem in that the likelihood of overlooking defects and the like in the cyclical pattern increases.

SUMMARY OF THE INVENTION

An object of the present invention is to provide a surface inspection method and a surface inspection apparatus that make it possible to detect defects and the like in one type of pattern or in a plurality of types of patterns formed on a test piece easily with a high degree of reliability and efficiency. A further object of the present invention is to provide a recording medium and a data signal that provide a surface inspection program executed by the surface inspection apparatus.

In order to attain the above objects, a surface inspection method according to the present invention for inspecting a pattern formed at a surface of a test piece, comprises: a first step in which a plurality of inspection conditions that are different from each other are set; a second step in which light from the surface of the test piece is detected by irradiating illumination light onto the surface of the test piece under each of the plurality of inspection conditions; a third step in which a plurality of sets of detection information corresponding to the plurality of inspection conditions are generated based upon the detected light; a fourth step in which a logical OR of the plurality of sets of detection information is obtained; and a fifth step in which a decision is made as to whether or not the pattern at the surface of the test piece is acceptable based upon results of the logical OR.

In this surface inspection method, preferably, in the third step: an image of the surface is formed by condensing at least one of specific diffracted light, scattered light and reflected light from the surface of the test piece under each of the plurality of different inspection conditions; the image is converted to an image signal; and the detection information is generated based upon the image signal.

Also, preferably, the pattern comprises a plural types of cyclical pattern; the plurality of inspection conditions are respectively set in correspondence to pitches of the plural types of cyclic pattern.

Also, preferably, the plurality of inspection conditions are each set by rotating the test piece around a specific axis of rotation to change an angle of incidence of the illumination light onto the test piece and a light-receiving angle of the light from the test piece.

Also, preferably, the plurality of inspection conditions are each set by moving a light source of the illumination light to change an angle of incidence of the illumination light and/or moving a position of a light-receiving device that receives the light from the test piece to reset a light-receiving angle.

Also, preferably, the plurality of inspection conditions are each set in conformance to a order of diffracted light corresponding to a specific pitch of the pattern on the test piece.

Also, preferably, the plurality of inspection conditions are each set by adjusting a wavelength of the illumination light.

Another surface inspection method for inspecting a pattern formed at a surface of a test piece, comprises: a first step in which a plurality of diffraction conditions that are different from each other are set; a second step in which diffracted light from the surface of the test piece is detected by irradiating illumination light onto the surface of the test piece under each of the plurality of diffraction conditions; a third step in which a plurality of sets of detection information corresponding to the plurality of diffraction conditions are generated based upon the detected light; a fourth step in which a condition which is other than the diffraction conditions and is outside design diffraction conditions determined in conformance to the pattern is set; a fifth step in which scattered light from the surface of the test piece is detected by irradiating the illumination light onto the surface of the test piece under the condition other than the diffraction conditions; a sixth step in which detection information corresponding to the condition other than the diffraction conditions is generated based upon the scattered light that has been detected; a seventh step in which a logical OR of the plurality of sets of detection information generated in the third step and the detection information generated in the sixth step is obtained; and an eighth step in which a decision is made as to whether or not the pattern at the surface of the test piece is acceptable based upon results of the logical OR.

A surface inspection apparatus according to the present invention that conducts an inspection of a pattern formed at a surface of a test piece, comprises: a stage that holds the test piece; an illumination device that irradiates illumination light onto the surface of the test piece; a light-receiving device that detects at least one of diffracted light, scattered light and reflected light from the test piece; a drive device the makes it possible to vary at least one of; an angle of inclination of the stage, a position of the illumination device and a position of the light-receiving device, in order to guide the light from the surface of the test piece to the light-receiving device under a plurality of different inspection conditions; and an arithmetic operation device that sets the plurality of inspection conditions, generates a plurality of sets of detection information in correspondence to the plurality of inspection conditions based upon the light detected by the light-receiving device, obtains a logical OR of the plurality of sets of detection information thus generated and makes a decision as to whether or not the pattern at the surface of the test piece is acceptable based upon results of the logical OR.

Another surface inspection apparatus that conducts an inspection of a pattern formed at a surface of a test piece, comprises: a first illumination device that irradiates illumination light onto the surface of the test piece at a first angle of incidence; a second illumination device that irradiates illumination light from a light source formed in a slit onto the surface of the test piece at a second angle of incidence larger than the first angle of incidence; a light-receiving device that detects light originating from the surface of the test piece; and an arithmetic operation device that generates first detection information based upon light originating from the surface of the test piece through irradiation by the first illumination device detected by the light-receiving device, generates second detection information based upon light originating from the surface of the test piece through irradiation by the second illumination device detected by the light-receiving device, obtains a logical OR of the first detection information and the second detection information and makes a decision as to whether or not the pattern at the surface of the test piece is acceptable based upon results of the logical OR.

A recording medium according to the present invention has a program employed in a surface inspection apparatus that conducts an inspection of a pattern formed at a surface of a test piece. And the program comprises: a first instruction for setting a plurality of different inspection conditions; a second instruction for detecting light originating from the surface of the test piece by irradiating illumination light onto the surface of the test piece under each of the plurality of inspection conditions; a third instruction for generating a plurality of sets of detection information corresponding to the plurality of inspection conditions based upon the detected light; a fourth instruction for obtaining a logical OR of the plurality of sets of detection information; and a fifth instruction for making a decision as to whether or not the pattern at the surface of the test piece is acceptable based upon results of the logical OR.

A data signal according to the present invention embodied in a carrier wave comprises a program employed in a surface inspection apparatus that conducts an inspection of a pattern formed at a surface of a test piece. And the program comprises: a first instruction for setting a plurality of different inspection conditions; a second instruction for detecting light originating from the surface of the test piece by irradiating illumination light onto the surface of the test piece under each of the plurality of inspection conditions; a third instruction for generating a plurality of sets of detection information corresponding to the plurality of inspection conditions based upon the detected light; a fourth instruction for obtaining a logical OR of the plurality of sets of detection information; and a fifth instruction for making a decision as to whether or not the pattern at the surface of the test piece is acceptable based upon results of the logical OR.

According to the present invention described above, by changing, for instance, at least, either the angle of incidence of illumination light relative to the surface of the test piece or the light-receiving angle at which the light from the surface is intercepted, a plurality of inspection conditions are set so that diffracted light, scattered light or reflected light can be detected under the individual inspection conditions. As a result, even when one type of cyclical pattern is formed on the surface and the intensity of the diffracted light of a given order from the cyclical pattern becomes lower due to thin film interference or the like, the presence of the cyclical pattern can be verified through a detection signal corresponding to the diffracted light generated under another inspection condition. It can be assumed that foreign matter is adhering or a defect is present in an area where the intensities of the individual detection signals are different from the intensities of signals corresponding to other areas. Then, based upon the logical OR of detection information (e.g., provided in the form of binary data) indicating individual defects and the like corresponding to the detection signals of the light detected under the plurality of inspection conditions, the distribution of defects and the like over the entire surface of the test piece can be ascertained.

If there are a plurality of types of cyclical patterns formed on the surface, on the other hand, a plurality of diffracted light fluxes having different diffracting directions are generated. When the intensity of the diffracted light originating from a specific cyclical pattern is low under a given inspection condition, for instance, settings may be made to ensure that diffracted light originating from the cyclical pattern under another inspection condition is received, and then by obtaining the logical OR of the individual sets of detection information, detection of defects and the like in the plurality of types of cyclical patterns can be achieved at once.

DESCRIPTION OF THE REFERRED EMBODIMENTS

First Embodiment

The following is an explanation of the first embodiment of the present invention given in reference to FIGS. 1 through 4. In this embodiment, the present invention is adopted in an inspection of a test piece, i.e., a wafer, conducted under a plurality of inspection conditions.

Figure 1:
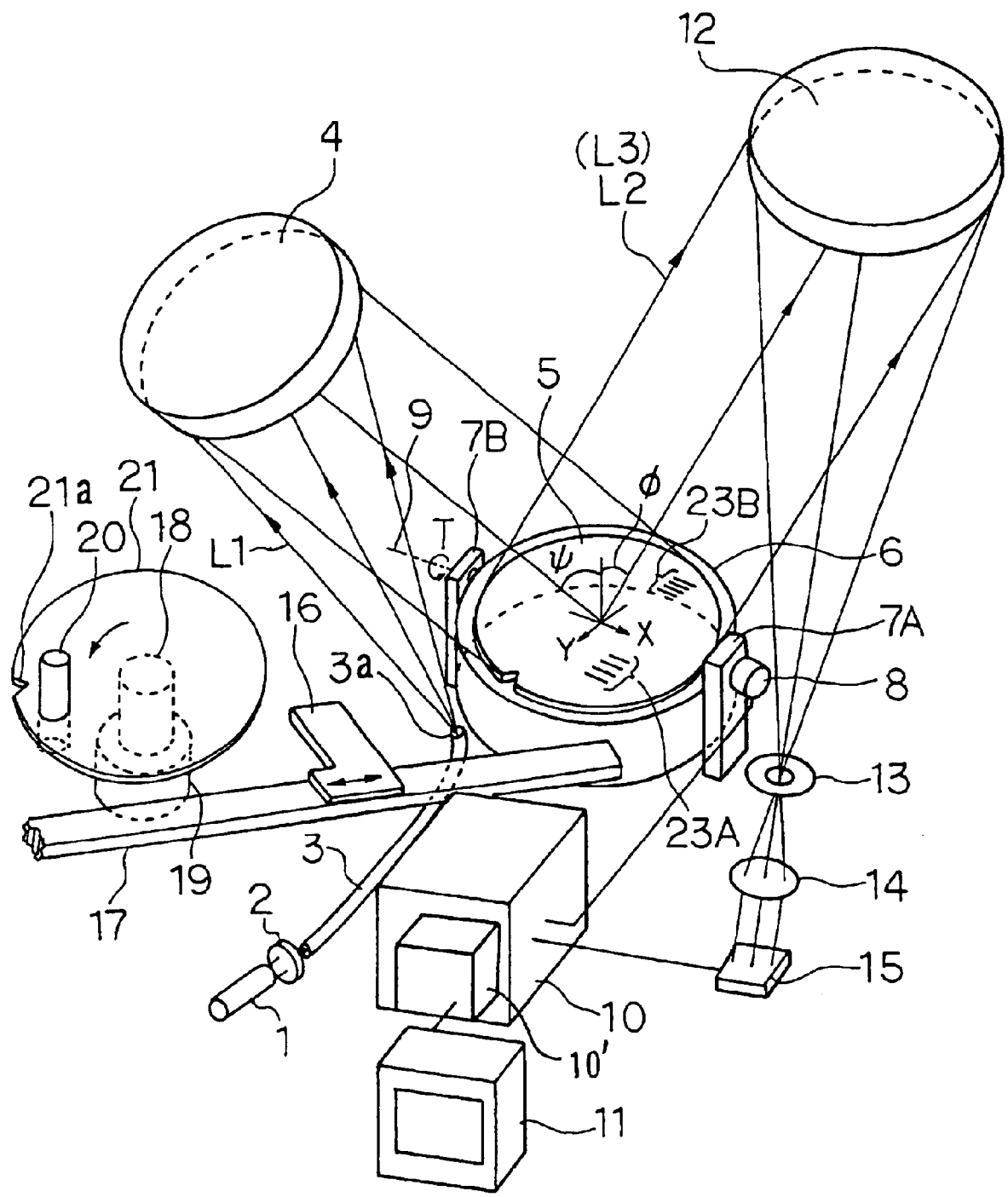
FIG. 1 is a perspective illustrating the schematic structure of the surface detection apparatus in a first embodiment of the present invention.

In FIG. 1, which illustrates a surface inspection apparatus in the first embodiment, light having a specific single wavelength (e.g., 546 nm, 436 nm or 365 nm) in the light emitted by a light source 1 constituted of, for instance, a discharge lamp (such as a metal halide lamp or a mercury lamp) or a halogen lamp is selected as illumination light L1 for inspection by a wavelength-selective filter such as an interference filter (not shown). The selected illumination light L1 is condensed at the entry end of an optical fiber bundle 3 by a condenser lens 2, and the illumination light L1 emitted through an exit end 3a of the optical fiber bundle 3 enters a concave mirror 4. The distance between the exit end 3a constituting a secondary light source and the concave mirror 4 is set approximately equal to the focal length of the concave mirror 4 (offsetting the axis, as explained later). The illumination light L1 reflected by the concave mirror 4 becomes an almost parallel light flux and enters the entire surface of a wafer 5 at an angle of incidence ψ. The light source 1—the concave mirror 4 constitute an illumination system (1–4).

The wafer 5 may be, for instance, a disc-shaped substrate constituted of a semiconductor (silicon or the like) or an SOI (silicon-on-insulator), with a notched portion for setting of rotating angle formed at its external circumference. In addition, the wafer 5 in the embodiment is a wafer for a specific ASIC, having circuit patterns formed over a plurality of layers through the preceding steps at its surface. The inspection apparatus in the embodiment inspects the position and size of foreign matter (or contamination) adhering to a circuit pattern and also the position and the size of a defect of the circuit pattern itself such as a line width error. In the following explanation, the axes in the orthogonal coordinate system at the surface of the wafer 5 are referred to as the X axis and the Y axis.

The wafer 5 is held onto a tilt stage 6 through, for instance, a vacuum method, and the tilt stage 6 is rotatably supported around a rotating shaft 9 which is parallel to the X axis between a pair of support plates 7A and 7B mounted on a base (not shown). A control system 10 constituted of a computer is capable of controlling the tilt angle (the angle of inclination) T of the tilt stage 6 via a drive motor 8 and, ultimately, is capable of controlling the angle of incidence ψ of the illumination light L1. In the state illustrated in FIG. 1, i.e., in the initial state, the surface of the tilt stage 6 (the surface of the wafer 5) is set to match the horizontal plane, with the tilt angle T in this initial stage set to 0°.

By irradiating the illumination light L1, diffracted light L2 of various orders including regular reflection light (diffracted light of 0 order) and scattered light L3 are generated at the pattern at the surface of the wafer 5. In this example, when detecting diffracted light L2 generated at an angle φ (hereafter referred to as a "light-receiving angle") around the X axis relative to the normal line at the surface of the wafer 5, the diffracted light L2 is reflected by a concave mirror 12 and reaches an aperture stop 13 having a circular opening. With the center of the circular opening of the aperture stop 13 placed at a position that practically matches the focusing position of the concave mirror 12, the aperture stop 13 blocks diffracted light other than the diffracted light achieving the light-receiving angle φ. The diffracted light L2 having passed through the aperture stop 13 forms an image of the entire surface of the wafer 5 at an image-capturing surface of a two-dimensional image-capturing element 15 such as a CCD via an image-forming lens 14. The image-capturing surface is set at the rear focusing position of the image forming lens 14, and an image signal having undergone photoelectric conversion at the image-capturing element 15 is provided to the image processing system 10' where the image signal is processed to detect foreign matter adhering to the surface of the wafer 5 and defects in the pattern, as explained later. A display apparatus 11 that displays information on defects and the like is connected to the image processing system 10'. The concave mirror 12~the image-capturing element 15 constitutes a light-receiving optical system (12~15). It is to be noted that in this embodiment, the scattered light L3 achieving a light-receiving angle φ may be detected as is to be detailed later. The control system 10 and the image processing system 10' comprise a microcomputer and its peripheral circuits. The control system 10 and the image processing system 10' may comprise microcomputers respectively.

At the illumination system (1~4) and the light-receiving optical system (12~15) in this embodiment, axes are offset to ensure that the optical members do not mechanically interfere with the tilt stage 6.

Figure 2:
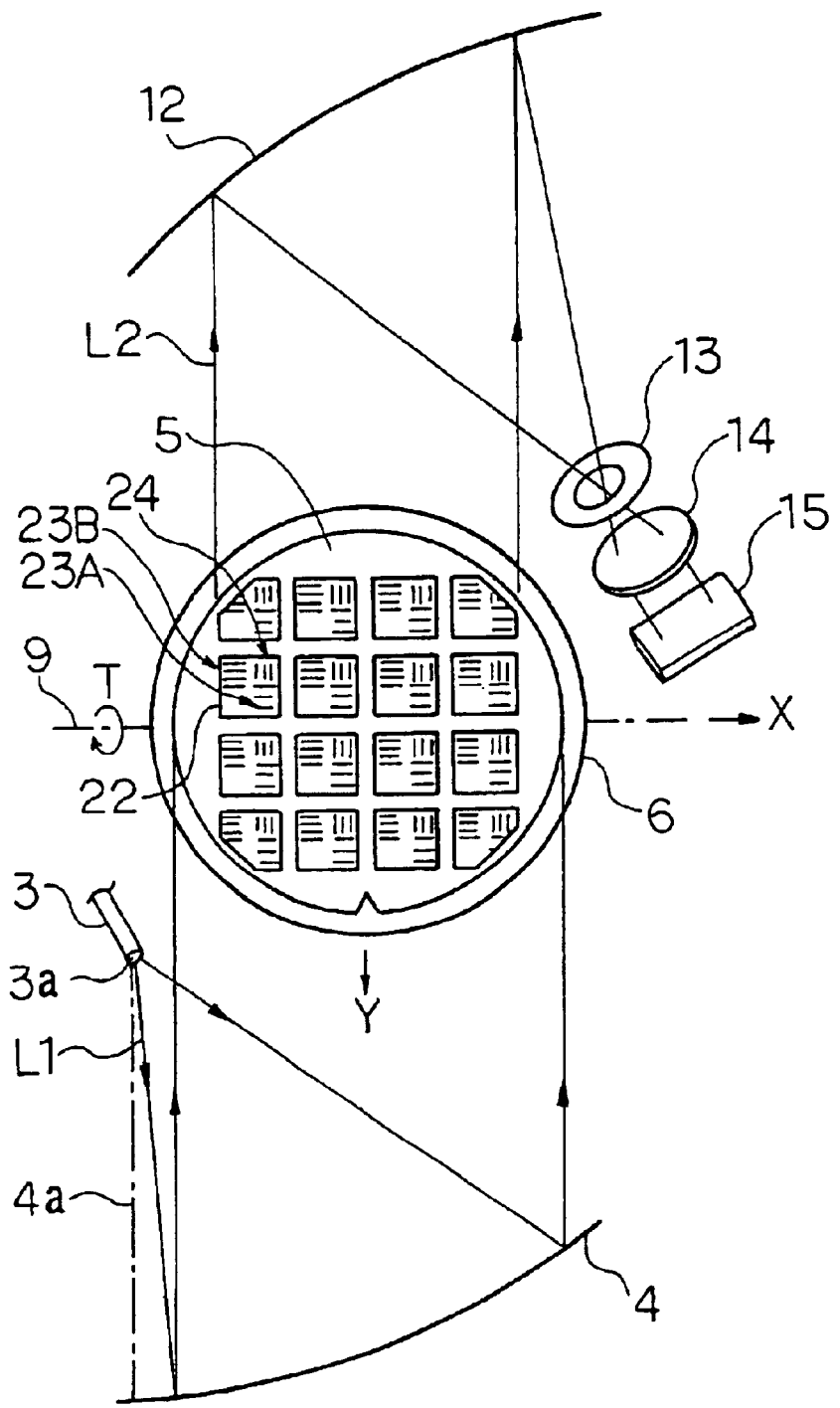
FIG. 2 is a plan view illustrating the relationships among the illumination system, the tilt stage 6 and the light-receiving optical system in FIG. 1.

In FIG. 2, which is a plan view illustrating the essential portion of the inspection apparatus in FIG. 1 in the initial state, the concave mirror 4 is a mirror having a reflecting surface constituting a paraboloid of revolution. In this state, an optical axis 4a of the concave mirror 4 is set so that its projection relative to the horizontal plane extends parallel to the Y axis and is offset from the tilt stage 6, with the exit end 3a constituting a secondary light source of the illumination light L1 is set at the focusing position on the optical axis 4a. In addition, the angle of the optical fiber bundle 3 is set so that the reflected light at the concave mirror 4 (its projection is parallel to the Y axis) irradiates the entire surface of the wafer 5. Likewise, the concave mirror 12 is a mirror having a reflecting surface constituting a paraboloid of revolution, with the projection of the optical axis of the concave mirror 12 set to extend parallel to the Y axis and offset from the tilt stage 6, and the center of the opening at the aperture stop 13 set at the focusing position of the concave mirror 12 on the optical axis. By offsetting the axes in this manner, the tilt stage 6 can be operated while ensuring that the surface of the wafer 5 can be illuminated at variable angles of incidence and with a parallel light flux achieving a consistent high illuminance and that the parallel light flux generated at a variable light-receiving angle from the wafer 5 can be condensed with a high degree of efficiency to form an image, without moving the optical systems (1~4) and (12~15) above the wafer 5.

It is to be noted that the concave mirrors 4 and 12 may be constituted by using, for instance, spherical mirrors in approximation or they may be each constituted by using a non-spherical mirror having undergone correction of various aberrations.

Again in reference to FIG. 1, since the tilt angle T of the wafer 5 is variable in this embodiment, the image formed on the image-capturing element 15 becomes extended or contracted along direction Y when the tilt angle T changes. Thus, at the image processing system 10', an image of the wafer 5 is first assembled on an image memory based upon an image signal from the image-capturing element 15, calculates the extending or contracting rate of the image of the wafer 5 in direction Y in correspondence to the current tilt angle T, implements magnification correction for the image along direction Y and correction of distortion which is generated by offsetting of the axes of the concave mirrors, and detects defects and the like using the image data having undergone the correction.

In addition, as illustrated in FIG. 2, the surface of the wafer 5 is divided into a plurality of shot areas 22 with a specific pitch along direction X and direction Y, and in each shot area 22, line shape patterns are repeatedly formed with one or more specific pitches. The repeated line shape patterns are so called a line-and-space pattern (hereafter referred to as an "L/S pattern"). Furthermore, each shot area 22 has a plurality of L/S patter areas, for example areas 23A, 23B and 24. The areas 23A and 23B have repeated patterns in direction Y which have different pitches from each other and the area 24 have repeated patterns in direction X. These L/S patterns 23A, 23B and 24 may be resist patterns with indentations and projections, or they may be formed by etching a specific type of metal film. Furthermore, a thin film such as a transparent protective film may be formed over these patterns. Since the projection of the illumination light L1 reflected by the concave mirror 4 enters the surface of the wafer 5 parallel to the Y axis, diffracted light L2 from the L/S patterns 23A and 23B arrayed along direction Y travels toward the concave mirror 12 so that its projection extends parallel to the Y axis. Consequently, through this arrangement, the L/S patterns 23A and 23B can be inspected. The wafer 5 needs to be rotated by 90° after the wafer 5 is back to a pre-alignment system explained later and then again to be placed on the tilt stage 6 to inspect the L/S pattern 24 arrayed along direction X.

Again, in reference to FIG. 1, a slider 17 is provided near the tilt stage 6 and a wafer arm 16 having a suction mechanism is provided slidably along the slider 17 so that the wafer 5 can transferred between the wafer arm 16 and the tilt stage 6. In addition, a rotating table 18, which is driven by a drive motor 19 to rotate or move along the vertical direction is provided near the slider 17, with a wafer 21 which is to be inspected next held through suction at the upper end of the rotating table 18. An image-capturing system 20 is provided along direction +Y relative to the rotating table 18, and the rotating table 18, the drive motor 19, the image-capturing system 20 and a control system (not shown) together constitute the pre-alignment system. The wafer arm 16 also engages in the delivery of the wafer between the rotating table 18 and the slider 17.

After the wafer 5 is inspected and carried out, for instance, the rotating table 18 is stopped at the angle at which the image-capturing system 20 has detected the position of a notched portion 21a at the external circumference of the wafer 21 and then the wafer 21 is delivered onto the tilt stage 6 via the wafer arm 16 to position the wafer 21 with its notched portion 21a facing toward direction +Y. In addition, if the wafer 21 is to be mounted with the notched portion 21a turned in direction +X, for instance, the rotating table 18 with the wafer 21 mounted on it needs to be further rotated by 90°. As explained above, the pre-alignment system achieves positioning with regard to the rotating angle of the wafer on the tilt stage 6.

Next, the principle that is applied when inspecting cyclical patterns at the surface of the wafer 5 by employing the inspection apparatus in the embodiment is explained. If the tilt stage 6 becomes inclined by the tilt angle T relative to the horizontal plane while the illumination system (1~4) and the light-receiving optical system (12~15) are in a fixed state in FIG. 1, the angle $\psi$ of incidence of the illumination light L1 entering the wafer 5 is ($\psi'$−T) and the light-receiving angle $\phi$ of the diffracted light L2 entering the light-receiving optical system is ($\phi'$+T), where the axis of the illumination system is at the angle $\psi'$ and the axis of receiving light is at the angle $\phi'$ respectively with the vertical line to the horizontal plane. The pitch p of a cyclical pattern (the L/S patterns 23A and 23B in this embodiment) from which the diffracted light L2 can be received at the light-receiving optical system needs to satisfy the following expression. It is to be noted that in the expression below, $\lambda$ represents the wavelength of the illumination light L1, n represents the order of diffraction (n is an integer) and the order n is 0 in the case of regular reflection.

$$\sin(\psi'-T)-\sin(\phi'+T)=n\cdot\lambda/p \tag{1}$$

Figure 7:
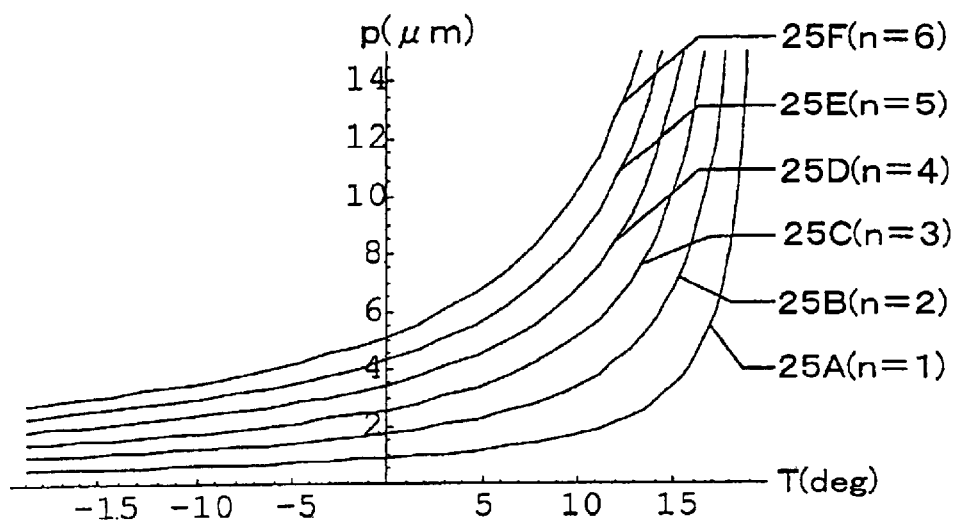
FIG. 7 illustrates the relationship between the tilt angle T and the pitch p of a pattern from which diffracted light of the first through sixth orders can be received in the first embodiment.

Since an integer value is assumed for the order n of diffraction, there may be conditions under which a plurality of pitches p corresponding to patterns that can be detected by the light-receiving optical system exist. FIG. 7 shows the orders of diffracted light that can be detected by varying the tilt angle T of the tilt stage 6 when the wavelength λ is approximately 550 nm, the angle ψ' of the axis of the illumination and the vertical line is 40° and the angle φ' of the axis of the light-receiving optical system and the vertical line is 0°.

In FIG. 7, the horizontal axis represents the tilt angle T (deg) of the tilt stage 6, the vertical axis represents the pitch p (μm) of a pattern from which diffracted light of up to the sixth order can be detected, and curves 25A~25F represent pitches p of patterns that can be detected at orders n of diffraction at 1~6. The factors indicating positional relation between the optical systems and the wafer 5 (light coming in/out angle conditions) are seen only in the left side of the expression (1). In other words, if the ratio of the order of diffraction to the pitch of pattern is not changed, the expression (1) is always satisfied. Since the order of diffraction is integer, the above means that diffracted light from patterns having pitches that are multiples of the pitch p achieved by multiplying it by an integer factor can also be detected. When the tilt angle T is at, for instance, 10° in FIG. 7, the pitch p of the pattern that can be detected is approximately 1.8 μm or an integer multiple of 1.8 μm. In addition, since the angle of incidence ψ' of the illumination system relative to the horizontal plane is 40°, the light that can be detected at the light-receiving optical system is regular reflection light (n=0) when the tilt angle T is at 20°. Since the right side of the expression (1) shows inverse proportion with the pattern pitch, as the tilt angle T approach 20° which is the regular reflection condition, the pattern pitch from which the diffracted light with each of orders can receive increases.

While a plurality of patterns having one of which is a multiple of another by an integer factor can be detected at the same tilt angle T, as explained above, it is assumed that the pitches p1 and p2 of the two L/S patterns 23A and 23B in FIG. 2 do not have a relationship whereby one of them is a multiple of the other by an integer factor in the wafer 5, which is a wafer for an ASIC (or a wafer for a logic IC or the like) in this embodiment. In such a case, assuming that light of the first order (n=1) is to be detected, the control system 10, for instance, calculates tilt angles T1 and T2 at which expression (1) is satisfied with p=p1 and p=p2. The control system 10 sequentially sets T1 and T2 for the tilt angle T of the tilt stage 6 and provides the values of T1 and T2 to the image processing system 10'. The image processing system 10' takes in the corresponding image signals from the image-capturing element 15 and forms an image of the entire surface of the wafer 5 on the image memory.

During this process, since the angle of elevation of the wafer surface varies at different tilt angles T, the ratio of the dimension of the image formed on the image-capturing element 15 along the direction (direction X) parallel to the rotating shaft 9 at the tilt stage 6 and the dimension along the direction (direction Y) perpendicular to the rotating shaft 9, changes. In order to correct for this change, the image processing system 10' multiplies the image on the image memory by sec (φ'+T) along the direction corresponding to direction Y for each tilt angle T. Then an image of an acceptable product that may be stored in advance at the image processing system 10', for instance is compared against the image of the wafer under inspection and their difference is determined to perform detection of foreign matter and defects by using the corrected image data. An area over which the difference between the images exceeds a specific value is identified as a defect.

In addition, foreign matter and defects may be detected through, for instance, pattern matching achieved by using various sets of image data to generate information that indicates the positions and sizes of defects and the like (hereafter referred to as "defect information"). The defect information generated in such a case is constituted of image data (one set of detection information) with a portion representing a normal pattern set to low level "0" and a portion representing a defect or the like set to high level "1". When the logical OR of the defect information corresponding to the individual tilt angles is ultimately obtained, a portion in which a defect or the like has been detected at a given tilt angle indicates high level "1" and, thus, defects and the like which have been detected in all inspection conditions can be detected over the entire surface of the wafer 5 using the logic OR.

Figure 3:
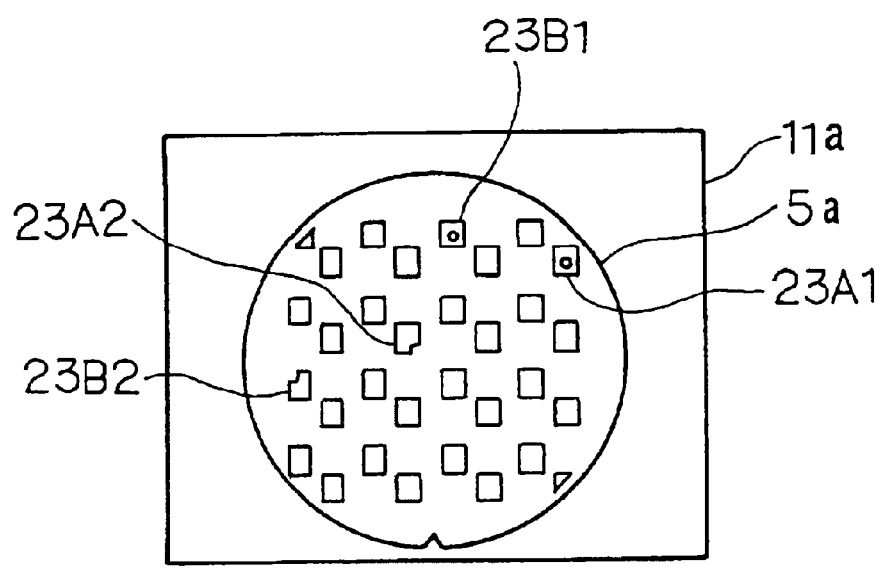
FIG. 3 presents an example of the results of an inspection conducted in the first embodiment.

The image processing system 10' provides information regarding defects over the entire surface of the wafer 5 that have been detected to a host computer (not shown). At the same time, the image processing system 10' provides the defect information, the logical OR of the defect information and image data of an image corresponding to the entire surface of the wafer 5 obtained at each of inspection conditions to the display apparatus 11 by converting them to another image signal. In response, an image 5a of the surface of the wafer 5 is displayed at a display unit 11a of a display apparatus 11 with portions corresponding to the images of the L/S patterns 23A and 23B under detection in FIG. 2 displayed inside the image 5a, as illustrated in FIG. 3. It is to be noted that images of the wafer 5 at individual inspection conditions may be composed to display it.

In FIG. 3, missing portions (dark portions) indicate foreign matter or defects in the areas 23A1 and 23A2 corresponding to the L/S pattern 23A having the pitch p1, and missing portions represent foreign matter or defects in the areas 23B1 and 23B2 corresponding to the L/S pattern 23B. Thus, by observing the image 5a, the operator can verify the position and size of any foreign matter or defect.

Figure 4:
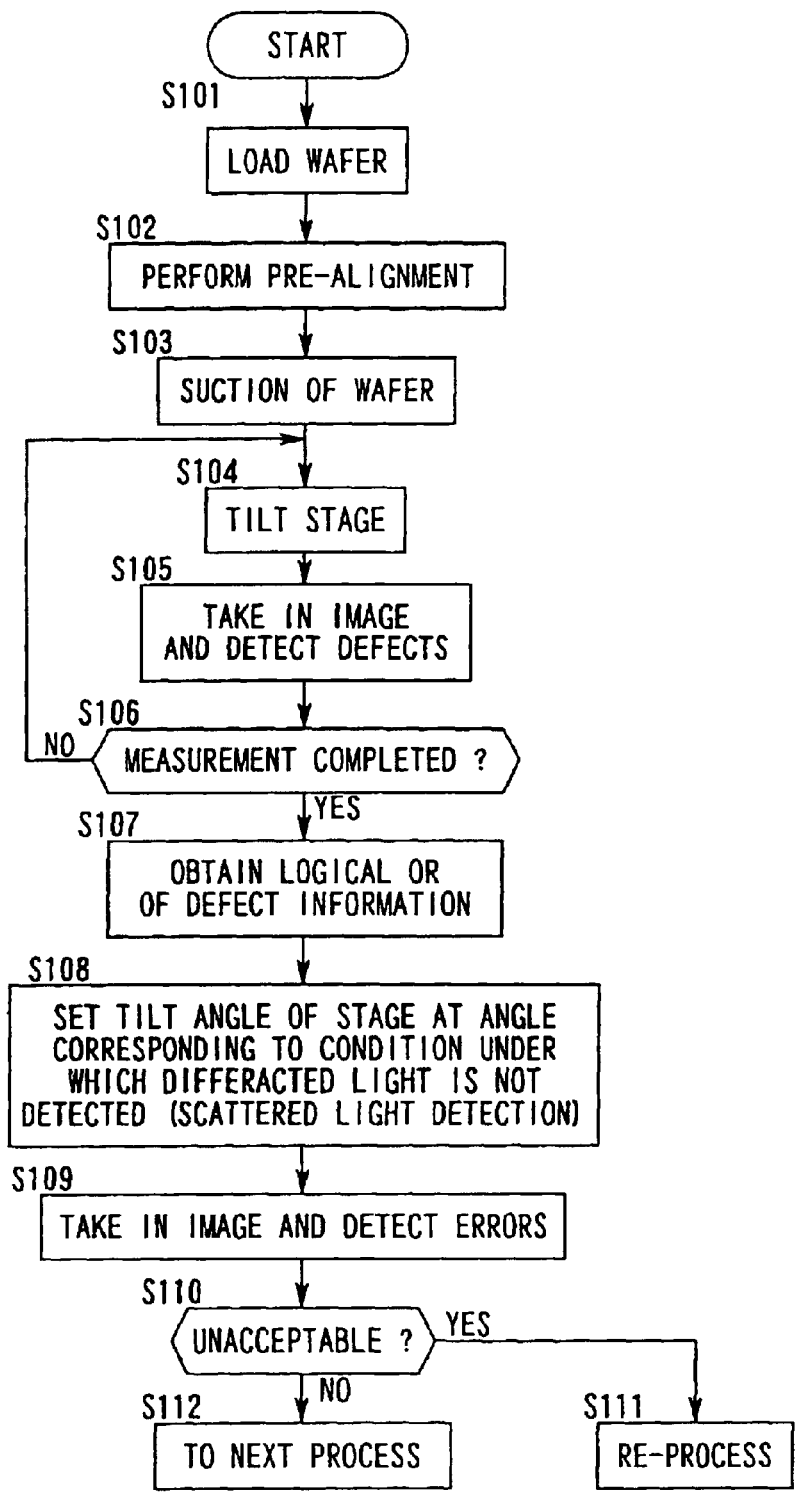
FIG. 4 is a flowchart of an example of the operation performed to inspect a wafer in the first embodiment.

Next, an example of the operation performed to actually inspect the wafer 5 in FIG. 1 by employing the surface inspection apparatus in the embodiment is explained in reference to the flowchart in FIG. 4. First, in step S101 in FIG. 4, a wafer to undergo inspection (wafer 5) is transferred from a wafer cassette (not shown) to the wafer arm 16 in FIG. 1 and then the wafer 5 is placed on the rotating table 18 of the pre-alignment system from the wafer arm 16. Next, in step S102, a pre-alignment is achieved by using the rotating table 18 and the image-capturing system 20 to position the notched portion of the wafer 5 facing along direction +Y, and then the operation proceeds to step S103, in which the wafer 5 is carried from the rotating table 18 onto the tilt stage 6 via the wafer arm 16 where the wafer 5 is held through suction. This sets the direction of the pitches (the direction of measurement) of the L/S patterns 23A and 23B to undergo inspection parallel to the projection of the illumination light L1 along the direction of entry and also parallel to the projection along the direction in which the light is received at the light-receiving optical system.

Next, in step S104, the control system 10 sets the tilt angle T of the tilt stage 6 at the angle T1 for the L/S pattern 23A having the pitch p1, and in step S105, it takes in an image signal from the image-capturing element 15, and the image processing system 10' builds up image data corresponding to one image plane using the image signal and implements magnification correction in correspondence to the tilt angle T1 before implementing defect detection. Then, a decision is made as to whether or not measurement has been completed at the tilt angles T1, T2, . . . , that have been set in advance (step S106) and if the measurement has not been completed, the next tilt angle T(k+1) is set (the operation returns to step S104) before taking in another image (step S105). In the embodiment, the tilt angle T is sequentially set at T1, T2 . . . .

Since there are no more tilt angles T to be set in this embodiment, the operation shifts from step S106 to step S107, in which the image processing system 10' calculates the logical OR of the binary image data (one set of which constitutes one set of defect information) corresponding to each of tilt angles T1 and T2. The logical OR of the image data corresponds to the logical OR of a plurality of sets of detection information according to the present invention. The image processing system 10' extracts defects in images corresponding to the individual conditions, and sets up a flag that is set to high level "1" at each of pixels constituting the image of the wafer when a defect has been detected. In addition, a flag is set to low level "0" in a pixel where there is no defect. The logical OR of the defect detection flags is calculated in the same pixel that has undergone inspections with different inspection conditions. A portion that ultimately indicates high level "1" represents a defect. The detection information and the like are sent to the host computer.

Next, in step S108, the control system 10 sets the tilt angle T of the tilt stage 6 at an angle that differs from the angles T1 and T2 at which the diffracted light from the L/S patterns 23A and 23B are detected by a specific order. It is to be noted that the tilt angle T must be set at an angle at which a diffracted light of the second order or higher from the L/S patterns 23A and 23B is not detected either. In other words, an inspection condition with which any diffracted light from patterns on the wafer 5 does not enter into the light-receiving optical system is set to receive scattered light from foreign matters on the wafer 5. In the next step S109, the image processing system 10' takes in an image signal from the image-capturing element 15, and after correcting the tilt angle, it converts the image data that have been obtained to, for instance, binary data by using a specific threshold value, extracts an area indicating high level "1" as an area with foreign matter or a scar and provides second defect information indicating the position and size of any foreign matter or scar to the host computer. Since scattered light is generated in an area where foreign matter is adhered and an area over which a defect has occurred, only the scattered light from the foreign matter or defect can be detected at a high SN ratio by detecting light from the wafer 5 at an angle at which diffracted light is not have been detected. Consequently, by executing steps 108 and 109, a defect such as foreign matter or a scar that may not be detected through the inspection conducted in steps 104~107 can be detected.

Next, in step S110, the host computer makes a decision as to whether the wafer 5 is acceptable or defective in conformance to a preset decision-making criterion, based upon the defect information corresponding to the entire surface of the wafer 5 provided by the image processing system 10'. If it is determined to be acceptable, the wafer 5 is sent to the next process (step S112), whereas if it is decided to be defective, the wafer 5 is sorted out either to be sent back for re-processing (step S111) or to be disposed of. If the L/S patterns 22 at the surface of the wafer 5 having undergone, for instance, the exposure and development processes are formed with resist patterns, the resist patterns may be peeled off, a photo-resist may be re-applied and exposed for re-processing (step S111) even if defects and the like are present in the resist patterns. By implementing re-processing in this manner, the yield of the wafer manufacturing process can be improved to achieve a reduction in production costs of semiconductor devices or the like.

In addition, it is desirable to store the image data of a wafer that has been sent to the next process after completing each inspection process, to enable tracking of the causes of the defects. Furthermore, it will make it possible to investigate the degree of influence of a defect on the performance of the product.

As explained above, in the embodiment, image data (individual sets of defect information at individual inspection conditions) are obtained by setting the tilt angle T of the tilt stage 6 at a plurality of angles in correspondence to a plurality of types of patterns to be detected, and information with respect to foreign matter or defects over the entire surface of the wafer is obtained based upon the logical OR of the sets of defect information. Thus, foreign matter and defects in the plurality of types of patterns can be detected quickly and accurately. It is to be noted that, the range of pitches of patterns that can be inspected in the embodiment is restricted by specific combinations of angles of incidence $\psi'$ of the illumination light from the illumination system (1~4) relative to the horizontal plane and the light-receiving angle $\phi'$ at the light-receiving optical system (12~15) relative to the horizontal plane. However, since no moving mechanism is provided above the wafer 5 in the inspection apparatus in the embodiment, the likelihood of foreign matter such as dust falling onto the wafer 5 in the inspection apparatus is low, achieving an advantage in that a fine pattern can be inspected with a high degree of accuracy.

As described above, while the embodiment is effective in applications in which a plurality of cyclical patterns having different pitches (pitches do not have a relationship whereby one is a multiple of another by an integer factor) are formed as in an ASIC, the inspection apparatus in the embodiment may also be employed to inspect a test piece such as a wafer for a DRAM, in which almost the entire surface is constituted of patterns having a consistent pitch. When inspecting a pattern achieving a consistent pitch (pitch p4), values T41~T46 for the tilt angle T corresponding to "n" set to, for instance, 1~6, in expression (1) are calculated to detect diffracted light of varying orders, these tilt angles T41~T46 are sequentially set as the tilt angle T of the tilt stage 6 in FIG. 1 and image signals at the individual tilt angles T41~T46 are taken in from the image-capturing element 15 to inspect the entire surface of the wafer. In addition, a defective portion may be set to indicate high level "1" and stored in memory as defect information obtained at the individual tilt angles through image processing, and the logical OR of the defect information having undergone conversion may be ascertained to be used as defect information for the wafer. For instance, if the pitch p4 is 4 $\mu$m, by setting the tilt angle T at 1.7°, 6.4° and 11° in FIG. 7, diffracted light of the fourth order (n=4), the third order (n=3) and the second order (n=2) from the pattern can be detected at these angles.

In this situation, assuming that a thin film is formed on the surface of the wafer, the intensity of the diffracted light of a specific order n may become lower or no diffracted light of the order n may be generated at all, depending upon factors such as the thickness of the thin film and the shape of the pattern to be inspected. Since intense diffracted light is obtained at, at least, one of the orders in the embodiment in which diffracted light of a plurality of orders (e.g., n=0~6) is sequentially detected, defects in the pattern undergoing detection can be detected with a high degree of reliability without an oversight even under such circumstances.

It is to be noted that while the illumination light irradiated on a test piece (wafer) has a single wavelength in the embodiment described above, light having a specific wavelength selectively extracted from illumination light having a plurality of wavelengths or illumination light within a specific bandwidth may be sequentially used to conduct an inspection by taking in an image of the test piece at each wavelength. In other words, in FIG. 1, the two wavelength selective filters (e.g., interference filters) provided at the illumination light path (the light path extending between the light source 1 and the concave mirror 4) in an interchangeable manner are sequentially set one at a time in the illumination light path to sequentially select illumination light with two specific wavelengths λ1 and λ2 in the light that contains a plurality of wavelengths and is emitted from the light source 1, and the illumination light with these two wavelengths are individually irradiated on the pattern having the pitch p on the wafer 5 sequentially so that when the illumination light with the wavelength λ1 is irradiated on the pattern at the water 5, an image of diffracted light of the n1th order resulting from the illumination light with the wavelength λ1 is captured and when the illumination light with the wavelength λ2 is irradiated on the pattern of the wafer 5, an image of diffracted light of the n2th order resulting from the illumination light having the wavelength λ2 is captured, sequentially at the image-capturing element 15. Since diffracted light from the pattern is diffracted in different directions even at the same order, if the wavelength varies, the following expression must be satisfied to ensure that diffracted light of the nth order does not overlap the diffracted light of the (n+1)th order when λ1<λ2.

$$(n+1)\lambda 1 > n\lambda 2 \quad (2)$$

In this case, since light that is diffracted along different directions in correspondence to varying wavelengths is received, it is necessary to reset the tilt angle T of the tilt stage 6 for each wavelength (every time the wavelength of the receiving light is changed), which necessitates magnification correction of the image in direction Y to be implemented in correspondence to the new tilt angle. Furthermore, when T1 and T2 represent the tilt angles T set to sequentially receive diffracted light of the n1th order resulting from the illumination light having the wavelength λ1 and diffracted light of the n2th order resulting from the illumination light having the wavelength λ2 respectively, the tilt angles must satisfy the following conditions relevant to the angle of incidence ψ at which the illumination light enters from the illumination system and the light-receiving angle φ of the light traveling to the light-receiving optical system.

$$\sin(\psi - T1) - \sin(\phi + T1) = n1 \cdot \lambda 1/p \quad (3)$$

$$\sin(\psi - T2) - \sin(\phi + T2) = n2 \cdot \lambda 1/p \quad (4)$$

It is assumed that in the inspection apparatus in FIG. 1, light fluxes corresponding to two different wavelengths, i.e., light having a wavelength of 550 nm (light with the wavelength λ1) and light having a wavelength of 630 nm (light with the wavelength λ2) are supplied from the light source 1 and that although not shown in FIG. 1, a first wavelength selective filter that selects the light having the 550 nm wavelength (the light with the wavelength λ1) and a second wavelength selective filter that selects the light having the 630 nm wavelength (the light with the wavelength λ2) are provided in the illumination light path extending between the light source 1 and the concave mirror 4 so that either one of them can be selectively set within the illumination light path by a drive system (not shown). The drive system that sets one of the two wavelength selective filters in the illumination light path in this structure is controlled by the control system 10. The light source system that supplies the illumination light and also varies the wavelength of the illumination light comprises the light source unit (light source 1) that supplies illumination light with a plurality of wavelengths, the two wavelength selective filters (means for wavelength selection) that are interchangeable with each other, the condenser lens 2 and the optical fiber bundle 3, and the condenser optical system that condenses the light from the light source system to illuminate the surface of the test piece is provided with the concave mirror 4. When inspecting a pattern with a pitch p at 0.7 μm on the wafer 5 placed parallel to the horizontal plane, the angle ψ' of the axis of the illumination light relative to the vertical line at 40° and the angle φ' of the axis of the light-receiving optical system relative to the vertical line at 0°, the tilt angle T is set to approximately −4.713° to receive first order diffracted light resulting from the light with a wavelength of 550 nm and the tilt angle T is set to approximately −8.612° to receive first order diffracted light resulting from the light with a wavelength of 630 nm. By setting the tilt angle T at these angles, the range over which the tilt stage 6 is moved can be reduced compared to the range over which the tilt stage 6 would have to move when the tilt angle T is set to approximately −36.735° to receive second order diffracted light resulting from the light having a wavelength of 550 nm. In addition, there is another advantage in that since interference conditions attributable to the thin film and the like at the surface of the wafer 5 change as the wavelength of the illumination light used for the inspection is switched, defects that cannot be detected at a given wavelength can be detected at another wavelength.

It is to be noted that while an example in which illumination light with a specific wavelength is selectively irradiated on the test piece by employing a means for wavelength extraction such as the wavelength selective filters is used in the explanation given above, a wavelength varying device (a means for wavelength change) (not shown) that makes it possible to vary the output wavelength of the light from the light source 1 by changing the input voltage, the input current or the like at the light source 1 shown in FIG. 1 may be provided instead to change the wavelength of the light itself output from the light source 1 to use light having this new wavelength as illumination light to irradiate the test piece. In such a case, the light source system that supplies the illumination light and also varies the wavelength of the illumination light comprises the light source unit (light source 1) which supplies the illumination light, the wavelength varying device (means for wavelength change) that makes it possible to vary the output wavelength of the light from the light source unit (light source 1), the condenser length 2 and the optical fiber bundle 3. In addition, the condenser optical system that condenses the light from the light source system and illuminates the surface of the test piece is provided with the concave mirror 4.

Furthermore, the wavelength of the illumination light may be varied by adopting a structure in which a plurality of different types of light sources (He—Ne laser light source, semiconductor laser element, lamp and the like) are employed, at least one dichroic mirror or the like is utilized to synthesize illumination light with different wavelengths from the plurality of different types of light sources and a means for wavelength selection such as a shutter is provided in the light path extending between each light source and the dichroic mirror. Also, a reflecting member such as a mirror may be provided to get into the optical path or withdraw from the optical path for selecting a desired wavelength light source. In the above structure, by opening only one of the plurality of shutters, illumination light with a specific wavelength can be selectively guided to the test piece. It is to be noted that in this case, the light source system that supplies the illumination light and varies the wavelength of the illumination light comprises a light source unit constituted of a plurality of light sources and, at least one dichroic mirror which supplies illumination light with a plurality of different wavelengths, the plurality of shutters (means for wavelength selection), the condenser lens 2 and the optical fiber bundle 3, and the condenser optical system that condenses the light from the light source system and illuminates the surface of the test piece is provided with the concave mirror 4.

While the explanation is given above on an example in which diffracted images of the test piece corresponding to the individual wavelengths are sequentially detected at the detection system by varying the wavelength of the illumination light emitted by the illumination system to illuminate the test piece, a structure that employs a light source for supplying illumination light that contains a plurality of wavelengths at which detection is to be performed or illumination light having a specific wavelength range to irradiate the illumination light containing the plurality of wavelengths or the illumination light having the specific wavelength range on the test piece and detection is performed in correspondence to the individual wavelengths at the detection system may be adopted instead. In case that diffracted light is detected, wavelength can be selected according to light-receiving angle of the light-receiving optical system. However, since diffracted light of higher order which has a different wavelength may mix in at an inspection condition of the illumination system, light-receiving optical system and the wafer as described above. Consequently, while it is not necessary to provide any wavelength selective filters, shutters or the like at the illumination system, it is desirable to assume a structure having a plurality of wavelength selective filters that can be selectively set one at a time in the detection light path at the detection system, in correspondence with the individual detection wavelengths.

Second Embodiment

Figure 5:
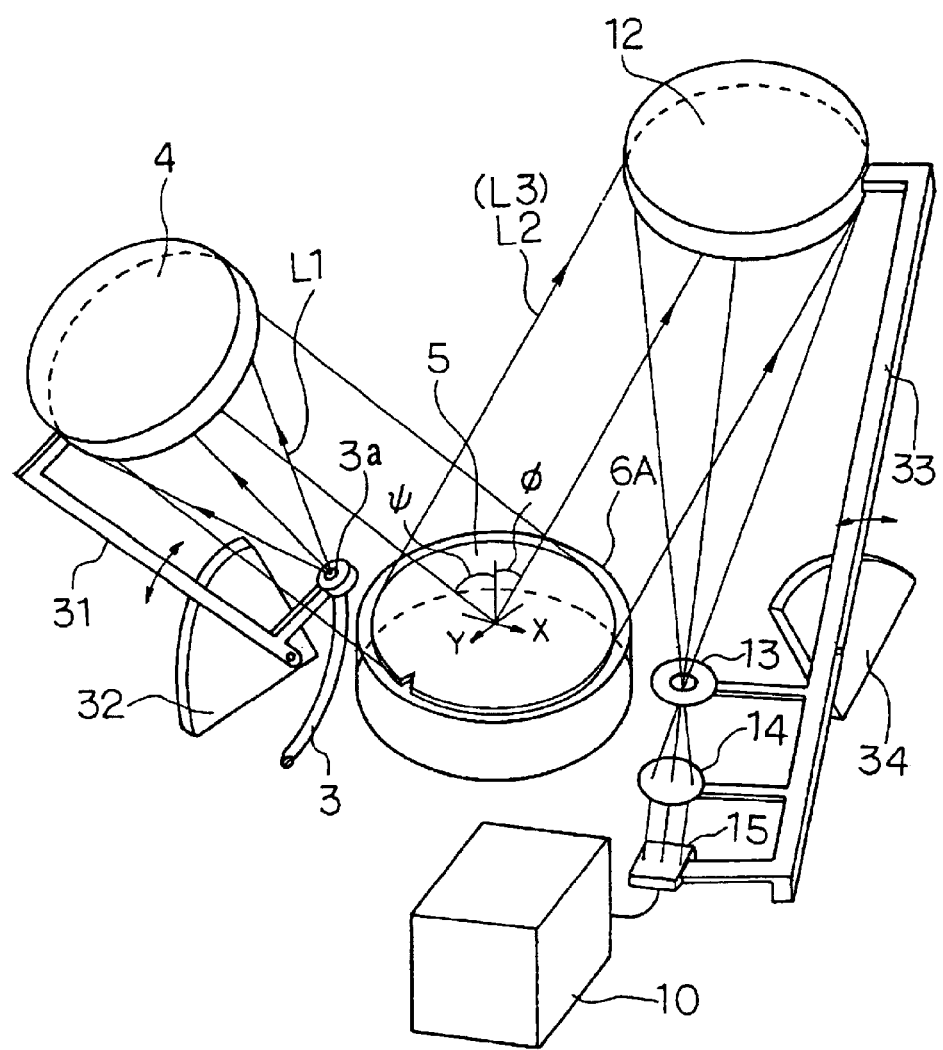
FIG. 5 is a perspective illustrating the essential portion of the surface inspection apparatus in a second embodiment of the present invention.

Next, the second embodiment of the present invention is explained in reference to FIG. 5. In this embodiment, the incidence angle of the illumination system and the light-receiving angle of the light-receiving optical system can be individually and independently varied, and the same reference numbers are assigned to components in FIG. 5 that correspond to those in FIG. 1 to preclude the necessity for a detailed explanation thereof.

In FIG. 5, which illustrates the essential portion of the surface inspection apparatus in the embodiment, the wafer 5, which constitutes the test piece, is held through suction onto a stage 6A and the stage 6A is secured onto a base (not shown). In addition, the exit end 3a of the optical fiber bundle 3 and the concave mirror 4 are secured at a support member 31 which is rotatably supported by a rotation drive mechanism 32 around a specific axis of rotation. Illumination light L1 is supplied to the optical fiber bundle 3 in FIG. 5 by the light source 1 and the condenser lens 2 in FIG. 1, and the illumination system (1~4) is essentially supported rotatably.

Likewise, the light-receiving optical system (12~15) that includes the concave mirror 12~the image-capturing element 15 is secured onto a support member 33 which is rotatably supported by a rotation drive mechanism 34 around a specific axis of rotation. In fact, the axes of rotation of the rotation drive mechanisms 32 and 34 are set to pass through an approximate center of the wafer 5 and a position near by focal points of the concave mirrors 4 and 12. In other words, the illumination system and the light-receiving optical system are provided in such a manner that they are capable of rotating essentially independent of each other in the embodiment. Also, since the exit end 3a of the optical fiber bundle 3, the wafer 5 and the aperture stop 13 of the light-receiving optical system are aligned almost in a straight line around the position near by the focal points of the concave mirrors 4 and 12, the entire wafer 5 can be illuminated and its image can be obtained regardless of the incidence angle of illumination light and the light-receiving angle of the light-receiving optical system. Other structural features are identical to those in the first embodiment.

In the embodiment, by rotating the illumination system, the angle of incidence $\psi$ of the illumination light L1 having a wavelength $\lambda$ which is irradiated from the concave mirror 4 onto the wafer 5 can be varied and, at the same time, by rotating the light-receiving optical system, the light-receiving angle $\phi$ of the diffracted light L2 (or scattered light L3) traveling from the wafer 5 toward the concave mirror 12 can be set independently of the angle of incidence $\psi$. As a result, the condition for receiving the diffracted light of the nth order (n is an integer which includes 0) from a cyclical pattern having a pitch p on the wafer 5 may be expressed as follows.

$$\sin \psi - \sin \phi = n \cdot \lambda / p \qquad (5)$$

In this embodiment, too, when inspecting a plurality of different types of patterns on the wafer 5, for instance, diffraction conditions corresponding to these different types of patterns are sequentially set to take in corresponding image signals from the image-capturing element 15. However, while a desired diffraction condition is set by rotating the tilt stage 6 in the first embodiment, a desired diffraction condition is set by rotating the illumination system and the light-receiving optical system in this embodiment. Thus, an advantage is achieved by adopting the second embodiment in that a higher degree of freedom is afforded in the selection of diffraction conditions compared to the first embodiment. In addition, since the light-receiving optical system can be utilized in a fixed state in which the angle of elevation of the wafer image formed on the image-capturing element 15 is constant, another advantage is achieved in that it is not necessary to implement magnification correction for the wafer image at the image processing system 10'. However, since the optical members (moving parts) constituting the light-receiving optical system move above the wafer 5 and this tends to generate foreign matter, it is desirable to position the moving parts as far away from the wafer 5 as possible.

Third Embodiment

Figure 6:
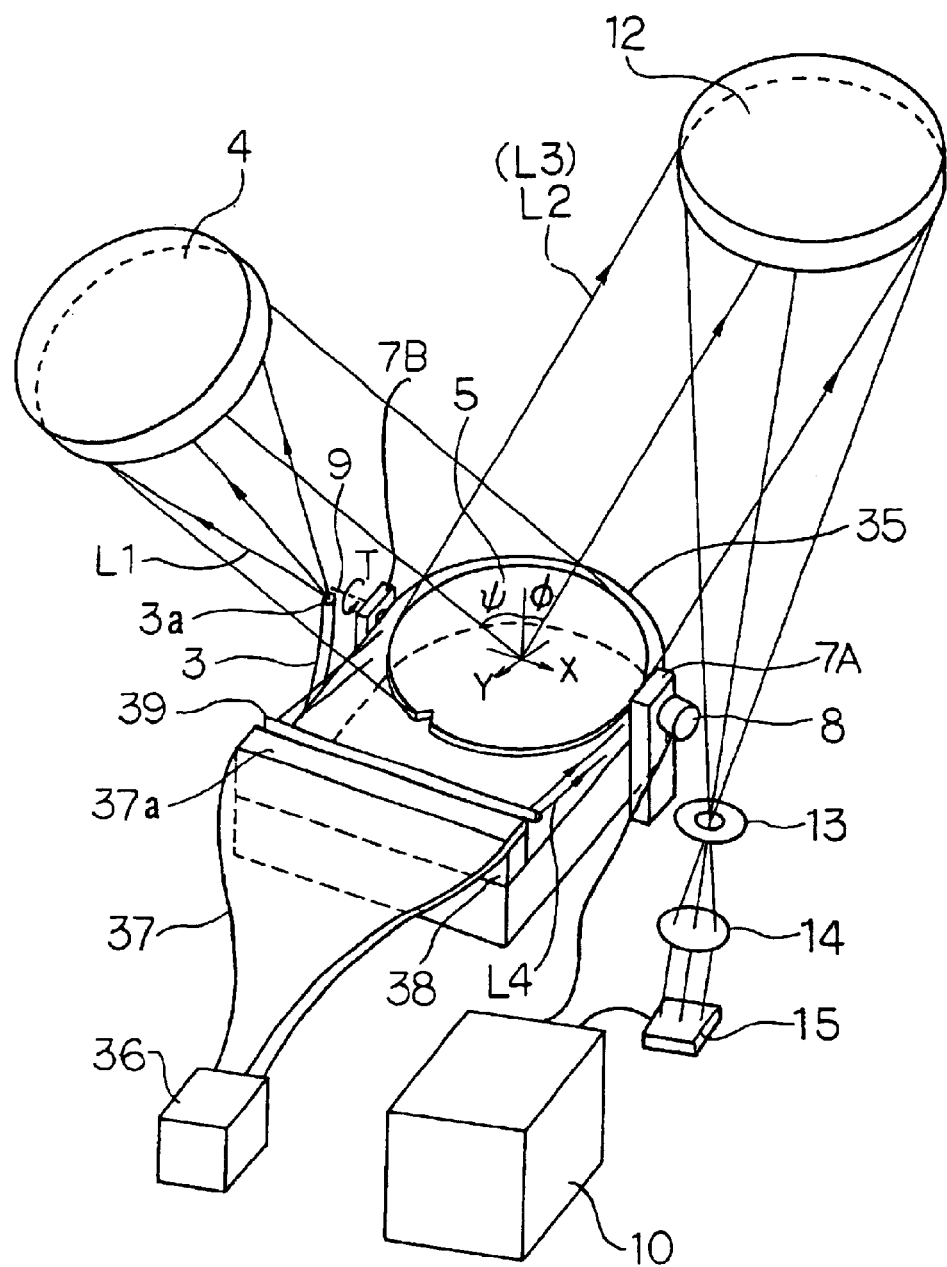
FIG. 6 is a perspective illustrating the essential portion of the surface inspection apparatus in a third embodiment of the present invention.

Next, the third embodiment of the present invention is explained in reference to FIG. 6. This embodiment is achieved by providing a second illumination system for illuminating the wafer at a large angle of incidence in addition to the illumination system (first illumination system) in the first embodiment, and the same reference numbers are assigned to components in FIG. 6 corresponding to those shown in FIG. 1 to preclude the necessity for a detailed explanation thereof.

In FIG. 6, which illustrates the surface inspection apparatus in the embodiment, the wafer 5 is held through suction onto a tilt stage 35, and the tilt stage 35 is rotatably supported by the drive motor 8 around the rotating shaft 9. In addition, as in the first embodiment, the wafer 5 is illuminated at an angle of incidence $\psi'$ by illumination light L1 generated by the first illumination system (1~4) which includes the optical fiber bundle 3 and the concave mirror 4 and diffracted light L2 (or scattered light L3) from the wafer 5 is intercepted at the light-receiving optical system (12~15) at a light-receiving angle $\phi'$, in a state in which the wafer 5 is aligned flush with the horizontal plane. In addition, illumination light generated within a light source 36 which is on the outside of the tilt stage 35 is condensed at an entry end of an optical fiber bundle 37 which fans out. An exit end 37a of the optical fiber bundle 37 has an elongated cross sectional shape extending straight along direction X, with the exit end 37a secured to the upper end of the tilt stage 35 via a spacer 38.

In addition, a cylindrical lens 39 which is elongated along direction X (lengthwise direction) and condenses light spreading in the direction (hereafter referred to as short-side-wise) perpendicular to the lengthwise direction is secured to the tilt stage 35 via a support member (not shown) in the vicinity of the light emitting surface of the exit end 37a. Illumination light L4 emitted through the linear light emitting surface of the exit end 37a is converted to an almost parallel light fluxes in the short-side-wise direction by the cylindrical lens 39 and illuminates the entire surface of the wafer 5 at a large angle of incidence within the range of approximately 70°~90°. The wavelength of the illumination light L4 is the same as that of the illumination light L1, and the light source 36, the optical fiber bundle 37 and the cylindrical lens 39 constitute a second illumination system (36, 37 and 39). Other structural features are identical to those in the first embodiment.

In the embodiment, when the tilt angle T of the tilt stage 35 changes, the angle of incidence of the illumination light L1 is at ($\psi'$-T) and the light-receiving angle at which the diffracted light L2 is received is at ($\phi'$+T). In addition, at the first illumination system (1~4), the cross sectional area of the light flux of the illumination light L1 from the concave mirror 4 is set at a large value to ensure that the entire surface of the wafer 5 can be illuminated even when the angle of incidence ($\psi'$-T) is at 0°, i.e., even through a perpendicular illumination. Thus, when the angle of incidence ($\psi'$-T) increases, the width of the light flux irradiated onto the wafer 5 is substantially reduced, resulting in reduced efficiency in the utilization of the illumination light L1. In addition, since the illuminance of the illumination light L1 on the wafer 5 becomes lower, there is a concern that the intensity of the image formed on the image-capturing element 15 may become reduced to lead to reduced S/N ratio and the sensitivity in the detection of foreign matter, defects and the like may become reduced due to the reduced S/N ratio. As a solution, the wafer 5 is illuminated by the illumination light L4 from the second illumination system (36, 37 and 39) if the angle of incidence ($\psi'$-T) at which the illumination light L1 enters the wafer 5 exceeds 70° in the embodiment. Since this ensures a high degree of efficiency in illumination even at a large angle of incidence, i.e., since it makes it possible to illuminate the entire surface of the wafer 5 at a high illuminance, the intensity of the image of the wafer increases to enable detection of defects and the like at a high SN ratio.

It is to be noted that since the second illumination system is secured onto the tilt stage 35, the angle of incidence $\psi$ of the illumination light L4 is constant. When the light-receiving angle at which diffracted light L2 from the wafer 5 with its surface flush with the horizontal plane is received is $\phi'$, the tilt angle T of the tilt stage 35 and the pitch p of a pattern that generates the diffracted light to be intercepted at the light-receiving optical system achieve a relationship expressed as follows.

$$\sin \psi - \sin \phi' = n \cdot \lambda / p \quad (6)$$

Figure 8:
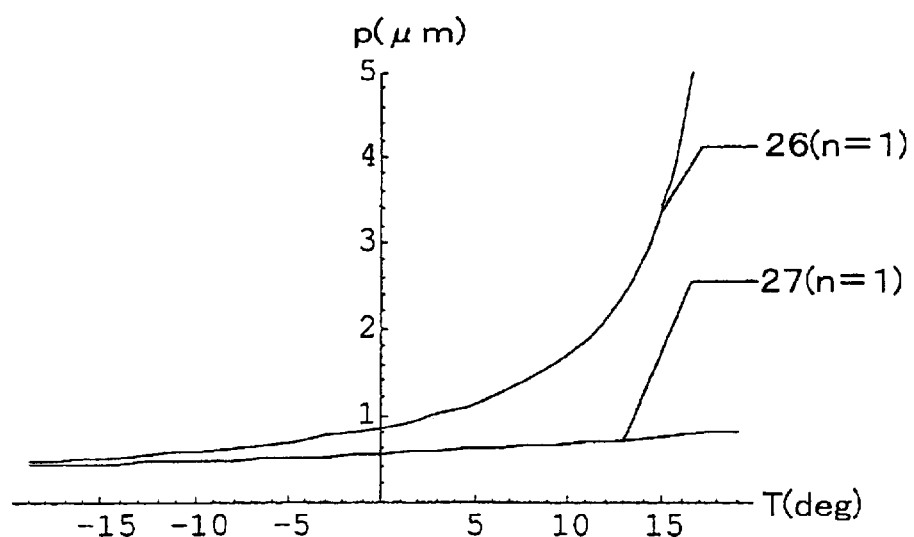
FIG. 8 illustrates the relationship between the tilt angle T and the pitch p of a pattern from which diffracted light of the first order can be received in the third embodiment.

A curve 27 in FIG. 8 represents the relationship between the tilt angle T(deg) and the pitch p($\mu$m) of the pattern from which a diffracted light (n=1) of the first order is detected based upon expression (6) when the second illumination system is employed. The relationship is achieved by setting the angle of incidence $\psi$ of the illumination light L4 from the second illumination system at 88° and the wavelength $\lambda$ of the illumination light at 550 nm. In addition, the first illumination system achieves a positional relationship identical to that in the first embodiment, with a curve 26 in FIG. 8 representing the relationship achieved between the tilt angle T and the pitch p of a pattern from which a diffracted light of the first order is detected, as does the curve 25A in FIG. 7 when the first illumination system is utilized. As the curve 27 indicates, by resetting the tilt angle T by approximately ±15°, diffracted light of the first order from a pattern having a pitch within the range of 0.4~0.8 $\mu$m can be detected at a high SN ratio when the second illumination system is utilized. As a result, it is desirable to use the first illumination system to detect a pattern having a pitch of approximately 1 $\mu$m or larger.

When actually conducting an inspection of the wafer 5 in FIG. 6, tilt angles Ta1, Ta2, . . . , to be set when the first illumination system is utilized and tilt angles Tb1, Tb2, . . . , to be set when the second illumination system is utilized are calculated by incorporating the pitch p of the pattern undergoing the inspection in expressions (1) and (6). Then, the first illumination system is caused to emit light, the tilt angle T of the tilt stage 35 is set to Ta1, Ta2, . . . and image signals are taken in from the image-capturing element 15 to conduct the inspection. Next, the second illumination system is caused to emit light, the tilt angle T of the tilt stage 35 is set to Tb1, Tb2, . . . and image signals from the image-capturing element 15 are taken in for an inspection. Then, finally, the logical OR of the defect information thus obtained needs to be ascertained.

It is to be noted that if two types of patterns such as a pattern having a pitch of approximately 0.8 $\mu$m or smaller and a pattern having a pitch of approximately 1 $\mu$m or larger, for instance, are formed on the wafer 5 the tilt angle T of the tilt stage 35 may be fixed at a specific angle that satisfies both expressions (1) and (6) to achieve an inspection of the two types of patterns within a very short period of time, simply by switching between light emission by the first illumination system and light emission by the second illumination system. Furthermore, an inspection may be performed to detect adhering foreign matter and a scar by using the second illumination system in a test condition where the diffracted light from patterns on the wafer does not enter into the light-receiving optical system.

It is to be noted that while the test piece is a wafer in the embodiment explained above, the present invention may be also adopted to inspect other types of test pieces such as a glass plate constituting a substrate for a liquid crystal panel and a photo mask (reticule). As explained above, the present invention is not limited to the embodiments described above, and may assume various different structures without deviating from the scope of the present invention.

In addition, while an explanation is given above in reference to the embodiments on an example in which two types of line-and-space patterns 23A and 23B having different pitches are inspected, it is not necessary to restrict the number of different types of patterns to two. It is obvious that the present invention may adopted to inspect more than two different types of patterns. In such a case, inspection conditions (or diffraction conditions) corresponding to the individual pitches should be set. More specifically, the tilt angle T of the wafer, the incidence angle $\psi$ of the illumination system, the light-receiving angle $\phi$ of the light-receiving optical system and/or the wavelength of the light from the light source should be adjusted in correspondence to the individual pitches.

Off-Axis Parabolic Mirror

Next, the concave mirrors 4 and 12 employed in the embodiments above are explained. As mentioned earlier, the concave mirrors 4 and 12 utilized in the embodiments are parabolic mirrors.

Figure 10:
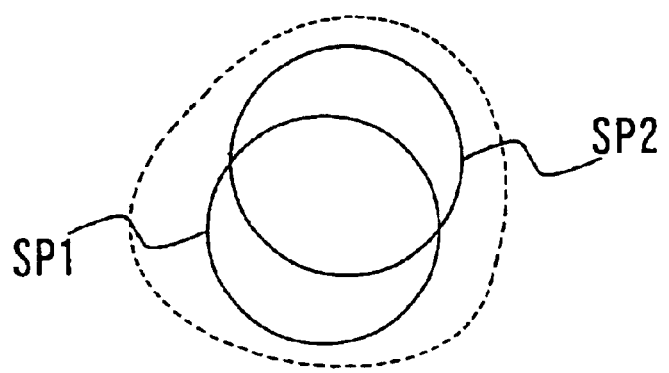
FIG. 10 illustrates the diffracted light fluxes at the entrance pupil when a spherical reflecting mirror is utilized.

In an apparatus in the prior art, due to the pupil aberration occurring in its decentered optical system achieved by employing a spherical reflecting mirror with the incident optical axis and the reflection optical axis not present on the same line, receiving light from the individual points on the substrate form images at positions that are different from each other at the aperture stop 13 which positions at the pupil position of the concave mirror. In FIG. 10, which illustrates this concept, the position of diffracted light SP1 originating from the center of the substrate and the position of diffracted light SP2 from an arbitrary point in the periphery are offset from each other on the pupil plane. The dotted lines indicate the size of the entire diffracted light flux. As illustrated in FIG. 10, diffracted light from individual points travels to different positions, and if a portion of the diffracted light is eclipsed due to the presence of an opening or the like, the light quantity of the light from only some points on the substrate becomes reduced instead of the light quantity corresponding to the entire substrate. The levels of diffracted light corresponding to the individual points on the substrate, i.e., the levels of SP1 and SP2 in FIG. 10, roughly correspond to the numerical aperture (NA) at the illumination optical system. Assuming that the numerical aperture (NA) at the light-receiving optical system is equal to the numerical aperture (NA) at the illumination optical system, the degree of lightness of the image varies depending upon the location, since the size of the pupil image (effective NA) that can be taken in by the light-receiving optical system varies depending upon the position on the substrate. This influences the sensitivity of the detection and results in a great reduction in the degree of reliability of the inspection.

Figure 9:
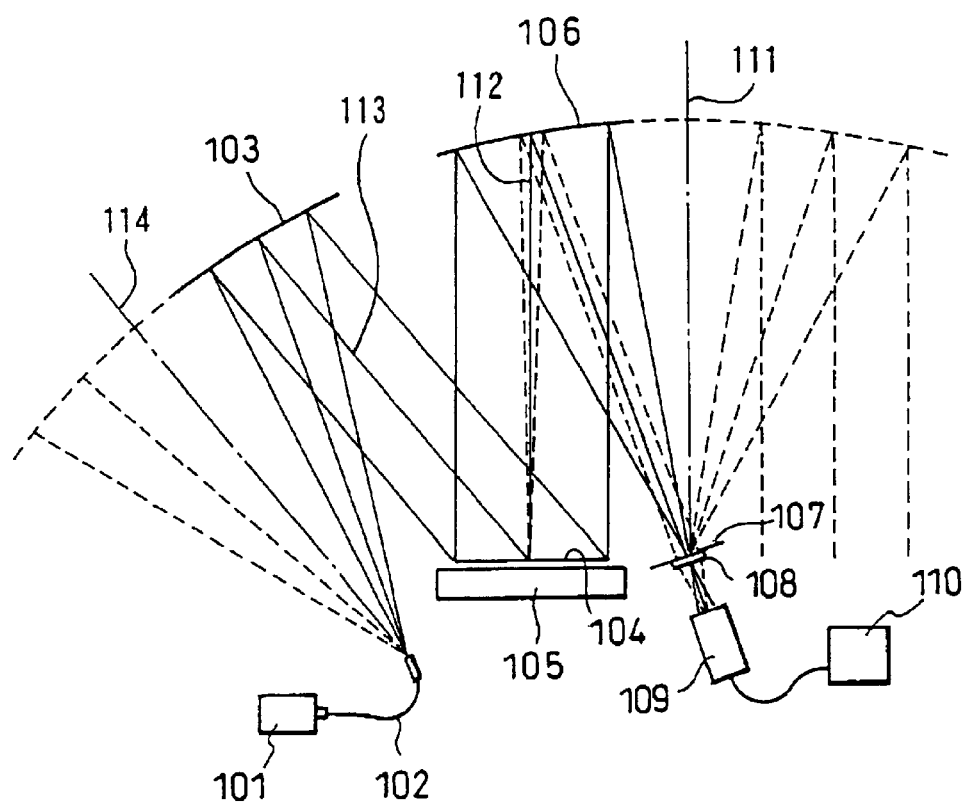
FIG. 9 illustrates the schematic structure of a surface inspection apparatus used to facilitate an explanation of the off-axis parabolic mirrors.

FIG. 9 illustrates a schematic structure of a surface inspection apparatus provided to facilitate an explanation of the off-axis parabolic mirrors. While it assumes a structure slightly different from that of the surface inspection apparatus in FIGS. 1 and 2, it basically adopts the same principle.

In FIG. 9, a lamp house 101 is provided with a light source and a lens (not shown), and the light from the light source is emitted through the end surface of a light guide 102 via the lens and light guide 102. In this structure, the end surface of the light guide 102 is located on the focal plane of a off-axis parabolic mirror 103, and the light that has been emitted illuminates a wafer 104 in an almost parallel light flux. The lamp house 101 is internally provided with a light source constituted of a halogen lamp, a metal halide lamp or the like and wavelength selective filters, and only light within a specific wavelength range is utilized as illumination light.

When the wafer 104 is illuminated, diffracted light (and/or reflected light) is generated from the illuminated wafer 104. The diffracted light to be received is condensed at a light-receiving optical system comprising a off-axis parabolic mirror 106 and a lens 108, so that a wafer image is formed on an image-capturing element 109 through the diffracted light.

The focusing position of the off-axis parabolic mirror 106 roughly matches the entrance pupil position at the lens 108, and the diffracted light is condensed at this position. While the condensed diffracted light is constituted of diffracted light of specific orders from the individual points at the wafer 104 that overlap one another, essentially no spherical aberration occurs since the off-axis parabolic mirrors are employed at the illumination optical system and the light-receiving optical system, and thus, the diffracted light from the individual points at the wafer 104 overlap with each other without any positional misalignment. Consequently, no local irregularity occurs even if a portion of the condensed diffracted light is eclipsed.

As shown in FIG. 9, the optical axis 111 of the off-axis parabolic mirror 106 is parallel to the optical axis 112 of the receiving light flux. An aperture diaphragm 107 is located at the focal point of the off-axis parabolic mirror 106. Furthermore, in the illumination optical system, the optical axis 114 of the off-axis parabolic mirror 103 is parallel to the optical axis 113 of the illumination light flux which illuminates the wafer 104.

In the above embodiments, the concave mirrors are used. However, a convex lens or an achromatic lens that has a positive refracting power may be used in the illumination optical system and the light-receiving optical system.

It is to be noted that in the embodiments described above, the processing is executed by a program internally provided at the control system 10. However, this program may be provided in a recording medium such as a magneto-optical disk. In addition, the program may be provided via a transmission medium such as a telecommunication line a typical example of which is the Internet. In other words, the program may be embodied in a signal on a carrier wave that carries a transmission medium and transmitted.

Figure 11:
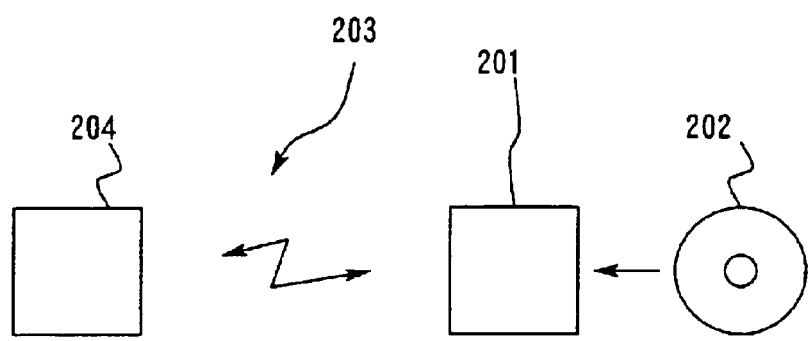
FIG. 11 illustrates how a program may be provided

FIG. 11 illustrates how this may be achieved. Reference number 201 corresponds to the control system 10 in FIG. 1 and is constituted of a computer. The computer 201 is provided with a drive device (not shown) that drives a magneto-optical disk 202, and is equipped with a function of connecting with a telecommunication line 203. A computer 204 is a server computer which provides, the program described above stored in it. The telecommunication line 203 may be a telecommunication line such as that for the Internet, a personal computer communication system or the like or it may be a dedicated telecommunication line. In addition, the telecommunication line 203 may be a telephone line or a wireless telephone line such as a line for a mobile telephone. The recording medium is not limited to the magneto-optical disk 202, and any of various types of recording media, including a CD ROM, a magnetic tape, a DVD and the like may be used.

What is claimed is:

1. A surface inspection method for inspecting a pattern formed at a surface of a test piece, comprising:

a first step in which a plurality of inspection conditions that are different from each other are set;

a second step in which light from the surface of the test piece is detected by irradiating illumination light onto the surface of the test piece under each of said plurality of inspection conditions;

a third step in which a plurality of sets of detection information corresponding to said plurality of inspection conditions are generated based upon an image of the surface formed by condensing specific diffracted light from the surface of the test piece under each of said plurality of different inspection conditions;

a fourth step in which a logical OR of said plurality of sets of detection information is obtained; and a fifth step in which a decision is made as to whether or not said pattern at the surface of the test piece is acceptable based upon results of the logical OR.

2. A surface inspection method according to claim 1, wherein in said third step:

an image of the surface is formed by condensing at least one of specific diffracted light, scattered light and reflected light from the surface of the test piece under each of said plurality of different inspection conditions;

said image is converted to an image signal; and said detection information is generated based upon said image signal.

3. A surface inspection method according to claim 1, wherein:

said pattern comprises a plural types of cyclical pattern;

said plurality of inspection conditions are respectively set in correspondence to pitches of said plural types of cyclic pattern.

4. A surface inspection method according to claim 1, wherein:

said plurality of inspection conditions are each set by rotating the test piece around a specific axis of rotation to change an angle of incidence of said illumination light onto the test piece and a light-receiving angle of the light from the test piece.

5. A surface inspection method according to claim 1, wherein:

said plurality of inspection conditions are each set by setting at least one of an angle of incidence of said illumination light, a light-receiving angle of the light from the test piece, and a wavelength of said illumination light.

6. A surface inspection method according to claim 1, wherein:

said plurality of inspection conditions are each set in conformance to an order of diffracted light corresponding to a specific pitch of the pattern on the test piece.

7. A surface inspection method according to claim 1, wherein:

said plurality of inspection conditions are each set by adjusting a wavelength of said illumination light.

8. A surface inspection method according to claim 1, wherein image data based upon the image of the surface of the test piece under each of said plurality of different inspection conditions is corrected according to the each of said plurality of different inspection conditions.

9. A surface inspection method for inspecting a pattern formed at a surface of a test piece, comprising:

a first step in which a plurality of diffraction conditions that are different from each other are set;

a second step in which diffracted light from the surface of the test piece is detected by irradiating illumination light onto the surface of the test piece under each of said plurality of diffraction conditions;

a third step in which a plurality of sets of detection information corresponding to said plurality of diffraction conditions are generated based upon the detected light;

a fourth step in which a condition which is other than said diffraction conditions and is outside design diffraction conditions determined in conformance to said pattern is set;

a fifth step in which scattered light from the surface of the test piece is detected by irradiating said illumination light onto the surface of the test piece under the condition other than said diffraction conditions;

a sixth step in which detection information corresponding to the condition other than said diffraction conditions is generated based upon the scattered light that has been detected;

a seventh step in which a logical OR of said plurality of sets of detection information generated in said third step and said detection information generated in said sixth step is obtained; and an eighth step in which a decision is made as to whether or not said pattern at the surface of the test piece is acceptable based upon results of the logical OR.

10. A surface inspection apparatus that conducts an inspection of a pattern formed at a surface of a test piece, comprising:

a stage that holds the test piece;

an illumination device that irradiates illumination light onto the surface of the test piece;

a light-receiving device that detects diffracted light from the test piece;

a drive device that makes it possible to vary at least one of; an angle of inclination of said stage, a position of said illumination device and a position of said light-receiving device, in order to guide the light from the surface of the test piece to said light-receiving device under a plurality of different inspection conditions; and an arithmetic operation device that sets said plurality of inspection conditions, generates a plurality of sets of detection information in correspondence to said plurality of inspection conditions based upon the light detected by said light-receiving device, obtains a logical OR of said plurality of sets of detection information thus generated and makes a decision as to whether or not said pattern at the surface of the test piece is acceptable based upon results of said logical OR.

11. A surface inspection apparatus according to claim 10, wherein said arithmetic operation device generates image data based upon the light detected by the light-receiving device under each of said plurality of different inspection conditions, and corrects the image data according to the each of said plurality of different inspection conditions.

12. A surface inspection apparatus that conducts an inspection of a pattern formed at a surface of a test piece, comprising:

a first illumination device that irradiates illumination light onto the surface of the test piece at a variable first angle of incidence;

a second illumination device that irradiates illumination light from a light source formed in a slit onto the surface of the test piece at a second angle of incidence larger than said first angle of incidence;

a light-receiving device that detects light originating from the surface of the test piece; and an arithmetic operation device that generates first detection information based upon light originating from the surface of the test piece through irradiation by said first illumination device detected by said light-receiving device, generates second detection information based upon light originating from the surface of the test piece through irradiation by said second illumination device detected by said light-receiving device, obtains a logical OR of said first detection information and said second detection information and makes a decision as to whether or not said pattern at the surface of the test piece is acceptable based upon results of said logical OR.

13. A recording medium having recorded therein a program employed in a surface inspection apparatus that conducts an inspection of a pattern formed at a surface of a test piece, said program comprising:

a first instruction for setting a plurality of different inspection conditions;

a second instruction for detecting light originating from the surface of the test piece by irradiating illumination light onto the surface of the test piece under each of said plurality of inspection conditions;

a third instruction for generating a plurality of sets of detection information corresponding to said plurality of inspection conditions based upon an image of the surface formed by condensing specific diffracted light from the surface of the test piece under each of said plurality of different inspection conditions;

a fourth instruction for obtaining a logical OR of said plurality of sets of detection information; and a fifth instruction for making a decision as to whether or not said pattern at the surface of the test piece is acceptable based upon results of said logical OR.

14. A recording medium according to claim 13, wherein image data based upon the image of the surface of the test piece under each of said plurality of different inspection conditions is corrected according to the each of said plurality of different inspection conditions.

15. A data signal embodied in a carrier wave comprising a program employed in a surface inspection apparatus that conducts an inspection of a pattern formed at a surface of a test piece, said program comprising:

a first instruction for setting a plurality of different inspection conditions;

a second instruction for detecting light originating from the surface of the test piece by irradiating illumination light onto the surface of the test piece under each of said plurality of inspection conditions;

a third instruction for generating a plurality of sets of detection information corresponding to said plurality of inspection conditions based upon an image of the surface formed by condensing specific diffracted light from the surface of the test piece under each of said plurality of different inspection conditions;

a fourth instruction for obtaining a logical OR of said plurality of sets of detection information; and a fifth instruction for making a decision as to whether or not said pattern at the surface of the test piece is acceptable based upon results of said logical OR.

16. A data signal according to claim 15, wherein image data based upon the image of the surface of the test piece under each of said plurality of different inspection conditions is corrected according to the each of said plurality of different inspection conditions.

* * * * *